(12) United States Patent
Frid

(10) Patent No.: US 8,192,484 B2
(45) Date of Patent: Jun. 5, 2012

(54) STENT FOR BLOOD FLOW IMPROVEMENT

(75) Inventor: Noureddine Frid, Beersel (BE)

(73) Assignee: Cardiatis S.A., Isnes (BE)

( * ) Notice: Subject to any disclaimer, the term of this patent is extended or adjusted under 35 U.S.C. 154(b) by 1226 days.

(21) Appl. No.: 11/708,962

(22) Filed: Feb. 20, 2007

(65) Prior Publication Data

US 2007/0162104 A1   Jul. 12, 2007

Related U.S. Application Data

(63) Continuation-in-part of application No. 10/450,315, filed as application No. PCT/BE01/00210 on Dec. 12, 2001, now Pat. No. 7,588,597.

(30) Foreign Application Priority Data

Dec. 12, 2000 (BE) .................................. 2000/0783
Mar. 13, 2001 (EP) .................................. 01870042

(51) Int. Cl.
*A61F 2/44* (2006.01)

(52) U.S. Cl. ...... 623/1.5; 623/1.51; 623/1.15; 623/1.44; 623/1.4

(58) Field of Classification Search .................. 623/1.15
See application file for complete search history.

(56) References Cited

U.S. PATENT DOCUMENTS

| | | | |
|---|---|---|---|
| 5,061,275 A | | 10/1991 | Wallsten et al. |
| 5,718,159 A | * | 2/1998 | Thompson .......................... 87/33 |
| 5,957,974 A | | 9/1999 | Thompson et al. |
| 6,004,346 A | * | 12/1999 | Wolff et al. ................. 623/23.71 |
| 6,099,561 A | * | 8/2000 | Alt ............................... 623/1.44 |

FOREIGN PATENT DOCUMENTS

| | | |
|---|---|---|
| EP | 0 804 902 A2 | 11/1997 |
| EP | 0 938 878 A2 | 9/1999 |
| GB | 1205743 | 9/1970 |
| WO | WO 99/55256 | 11/1999 |

OTHER PUBLICATIONS

EPO International Search Report, dated Jun. 12, 2003.

* cited by examiner

*Primary Examiner* — Thomas J Sweet
*Assistant Examiner* — Christopher D Prone
(74) *Attorney, Agent, or Firm* — Christie, Parker & Hale, LLP

(57) ABSTRACT

Luminal endoprosthesis formed of a multi-layer braided framework. The framework is devoid of any cover layer, and formed of a plurality of stabilized layers of biocompatible metal wires which are interlaced, forming a lattice, a plurality of wires of a given layer being integrated in the lattice of the adjacent layers. The mechanical characteristics of an outermost layer is so that when in place, the layer applies against a vessel wall, the other layers extending substantially along cylindrical surfaces distinct from the outermost layer so as to form a multi-layer mat which affects the haemodynamic of a flow of blood passing along or through this mat and preventing a growing of plaque.

6 Claims, 8 Drawing Sheets

*Fig 4*
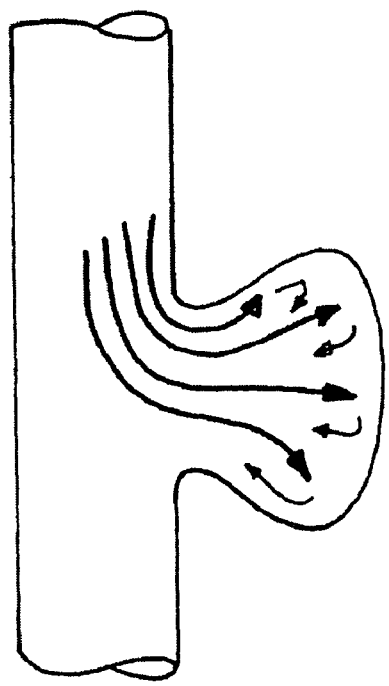
*Fig 5*
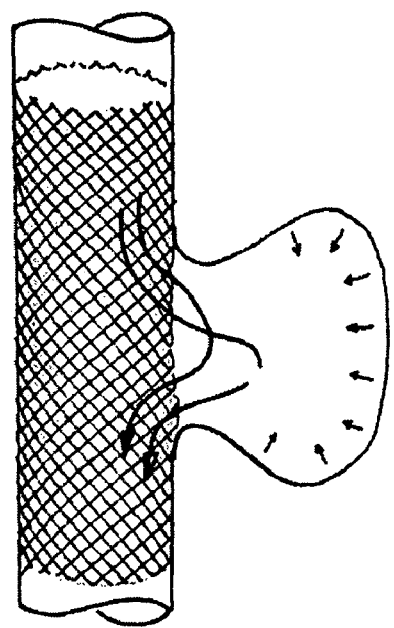
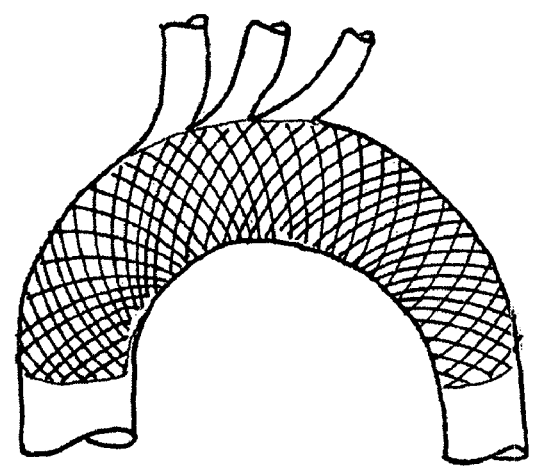
*Fig 3*

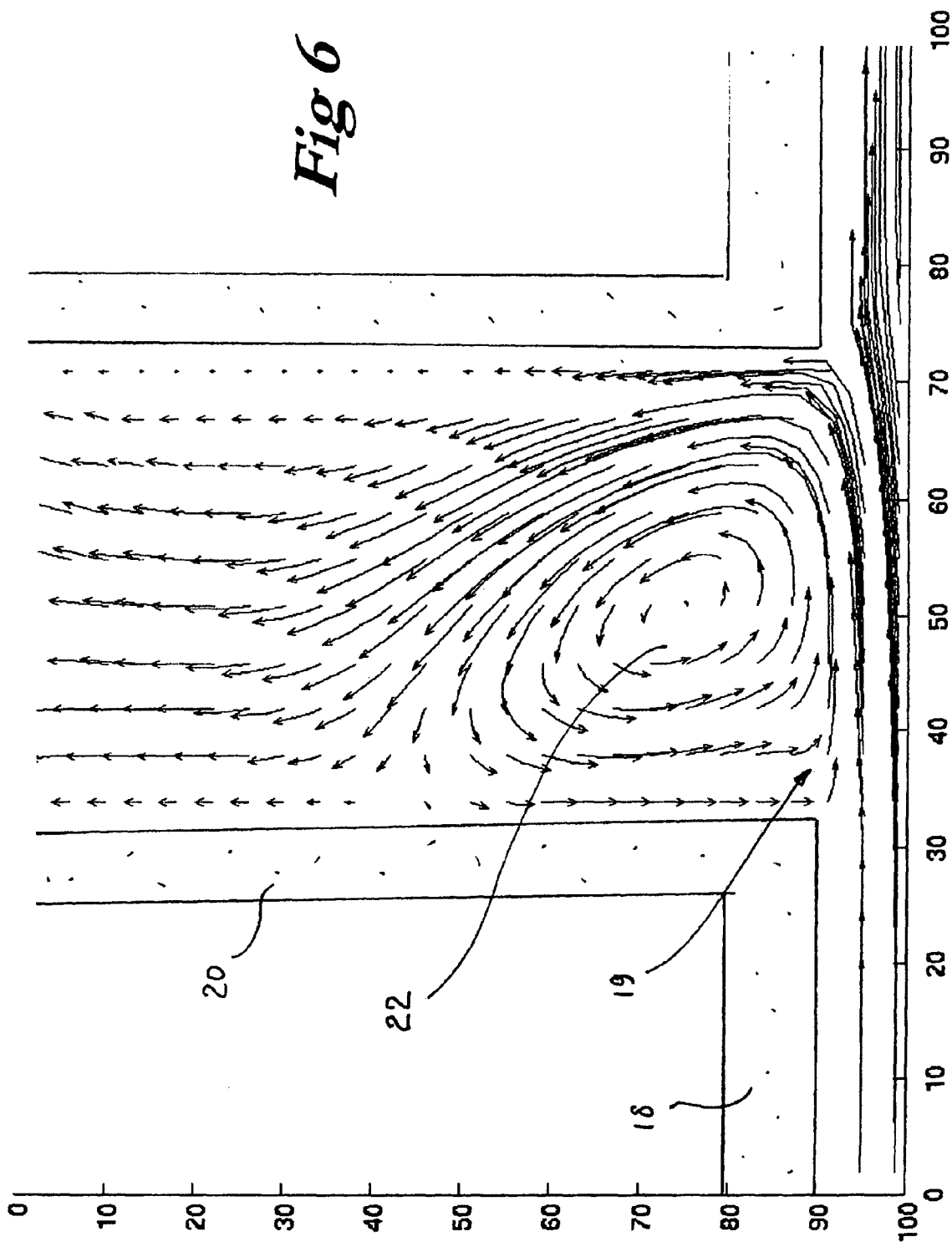

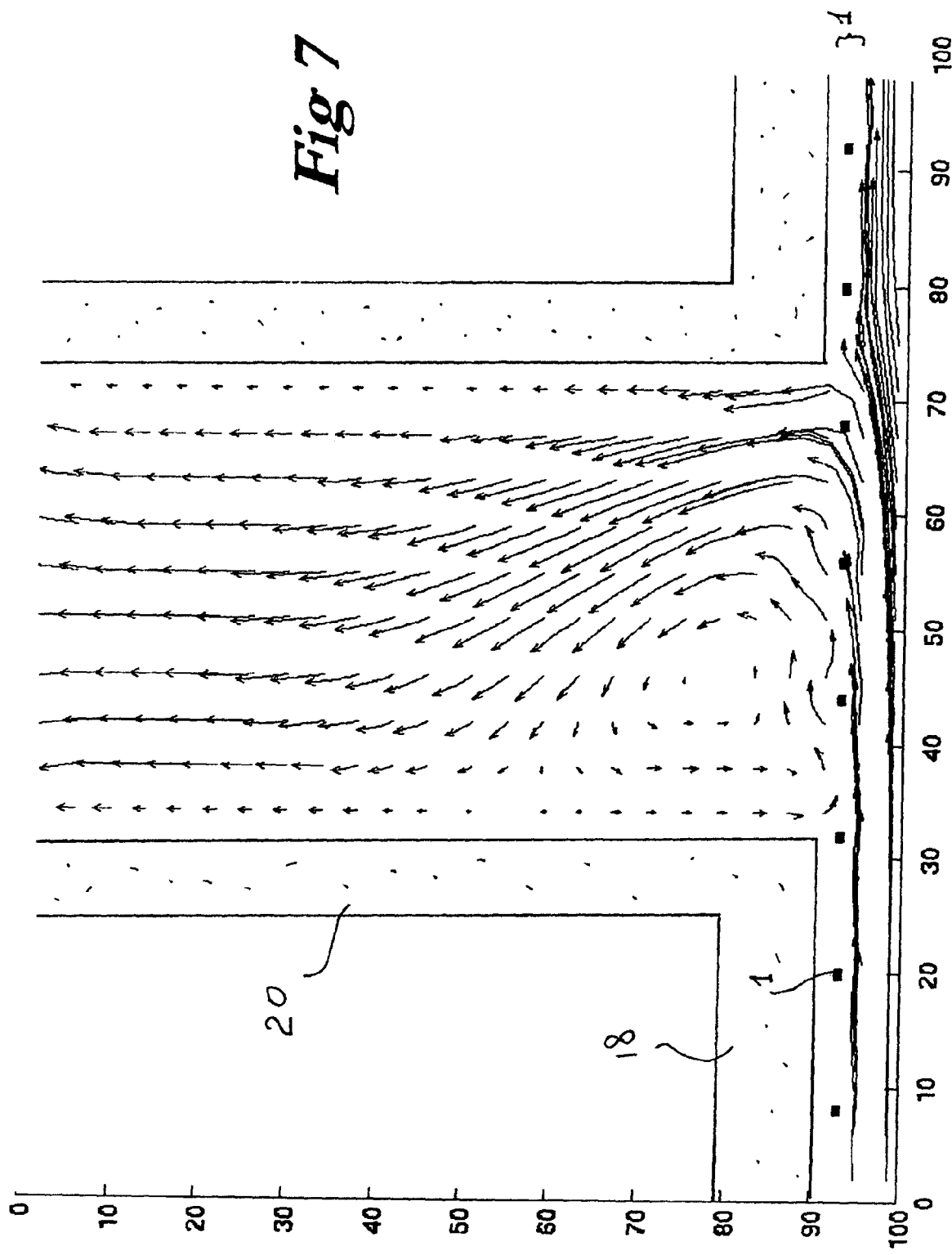

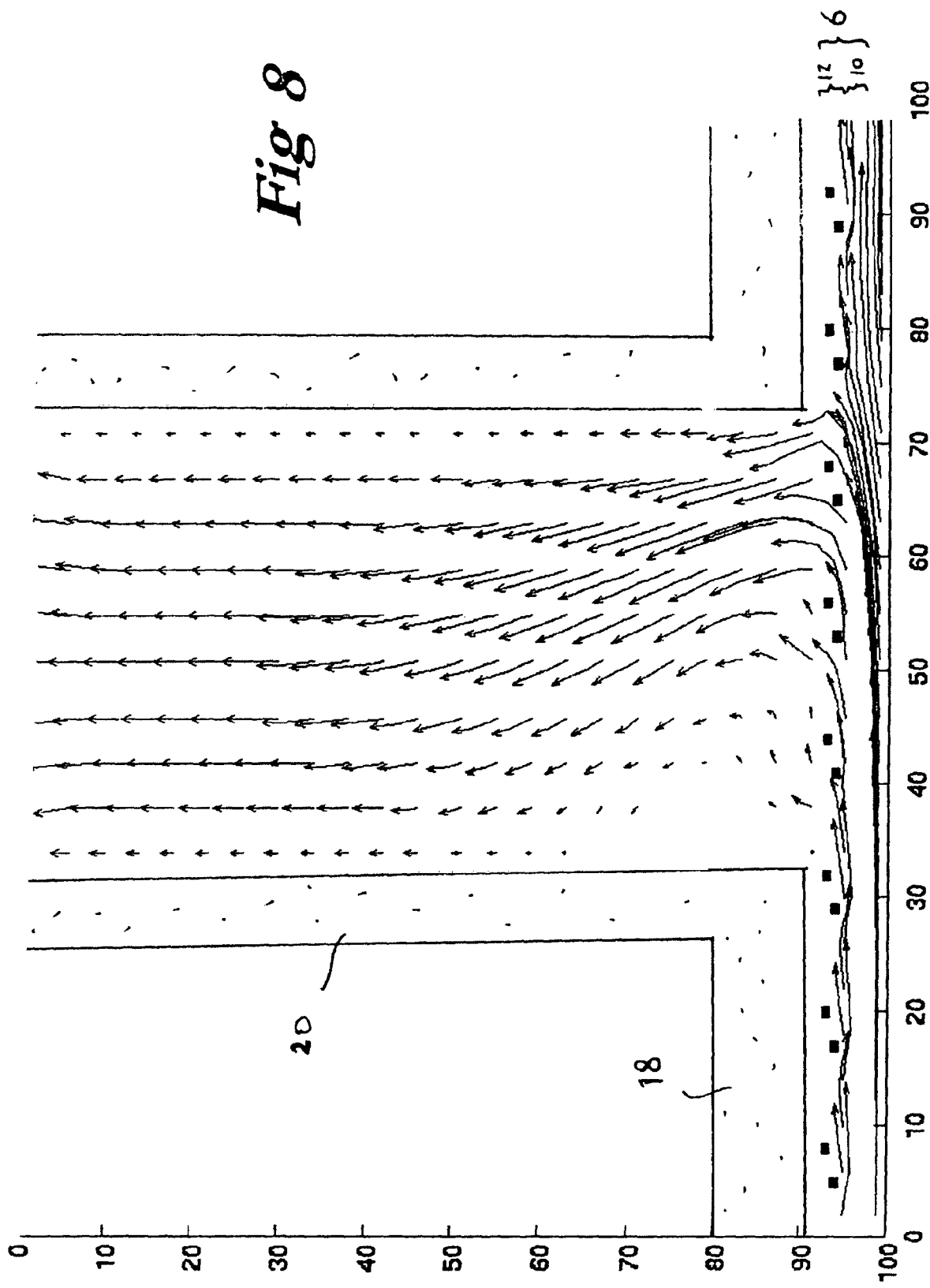

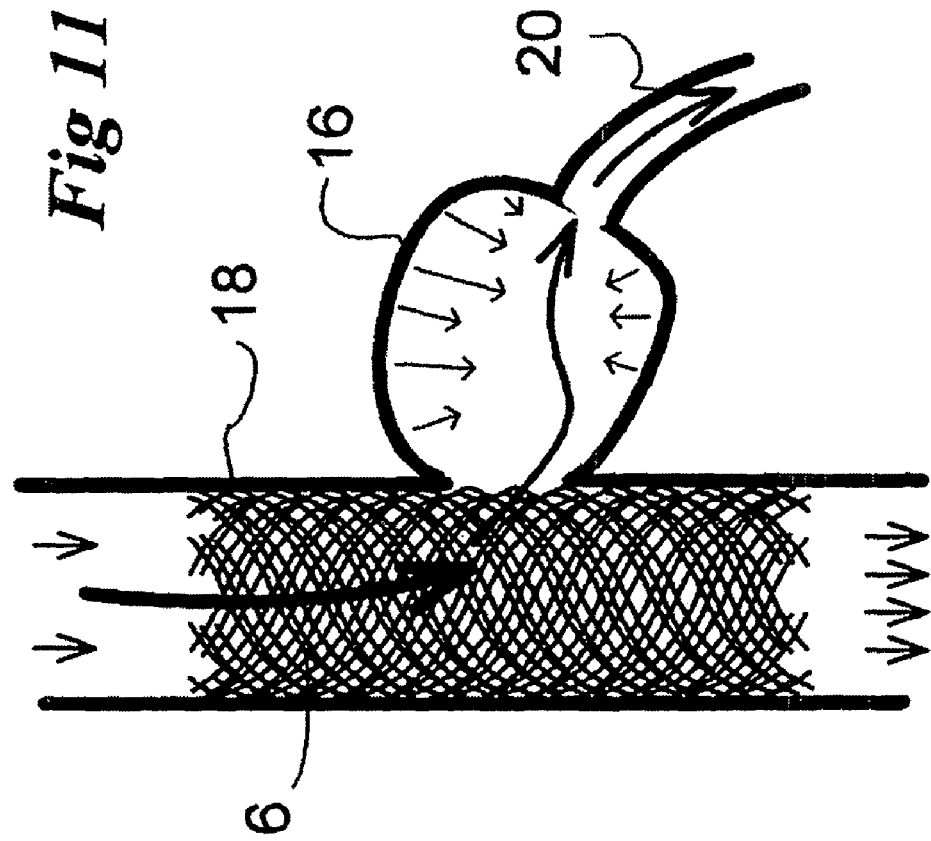
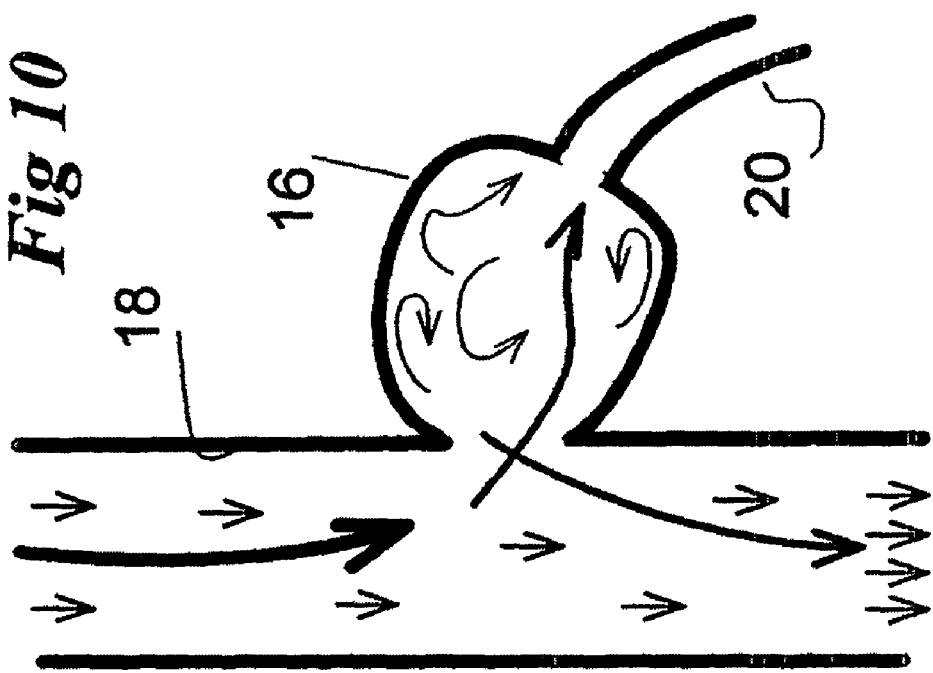

STENT FOR BLOOD FLOW IMPROVEMENT

CROSS-REFERENCE TO RELATED APPLICATION(S)

The present application is a continuation-in-part of U.S. patent application Ser. No. 10/450,315 filed Nov. 21, 2003, now U.S. Pat. No. 7,588,597 B2, which is the National Stage of International Stage of International Application No. PCT/BE01/00210 filed Dec. 12, 2001.

BACKGROUND OF THE INVENTION

1. Field of the Invention

The invention relates to luminal endoprostheses formed principally of a framework, without textile covering, generally called "stents", and more particularly to stents for blood vessels, and i.a. for blood vessels bearing junctions.

2. Description of the Related Art

Over the years, the implantation of luminal endoprostheses has become an approved technique for treatment of aneurysms, atherosclerosis, etc.

However, one crucial problem has still not been solved: namely that of perfectly matching the mechanical and hemodynamic characteristics of these endoprostheses and of the arteries in which they are implanted.

Even if very particular care has been taken to meet these criteria at the time of implantation, a disparity invariably develops in the long term. This is because the human body is subject to changes due to aging, while the endoprosthesis has a problem of stability over the course of time: tearing of the filaments, deterioration of the structure, possible increase in diameter (by loosening of the structure) and inadequate interaction with the flow.

The mechanical characteristics of a stent are determined essentially by the structure of its framework. Although different types of these exist, such as the frameworks made up of flat braids described in WO 99/55256, the most suitable framework at present is the cylindrical braided framework, such as is described in particular by Didcott in GB-1205743, or in U.S. Pat. No. 5,061,275.

This type of framework compresses easily for insertion, resists well to crushing and retains a relative flexibility compatible with that of the blood vessels; the structure adapts to the sinuous course of the rigid arteries to be treated.

To date, investigations into finding the optimum framework have focused on the choice of material, the braiding pitch, etc. These investigations inevitably come up against a number of practical problems. By adopting a very small braiding pitch (the angle between the axis and the spirals being close to 90° or by choosing thick wires, the radial force (resistance to crushing) is increased, which means a high rate of shortening. Conversely, a large pitch, where the angle formed between the axis and the spirals is close to 30° for example, and the use of thin wires give the framework good flexibility but a low resistance to crushing and thus a low radial force to resist to artery compression. This problem is even more critical for stents and endoprostheses made up of several modules cut by laser.

Attempts have been made, particularly by Thompson (U.S. Pat. No. 5,718,159), to combine metal wires with textile fibres. However, the results obtained are not convincing: the metal filaments deform the structure and, along their helical course, they create dislocations and spacing of the textile fibres. The fibres are subjected to stresses under the effect of the pulsations caused by the blood flow and they are subject to rapid erosion-fatigue by friction against the metal filaments (whose modulus of elasticity and diameter are greater). Furthermore, Thompson suggests to use for his endoprosthesis a framework made out of mere metal ("structural") filaments, covered by one or two impervious layers. This suggestion is purely theoretical. Indeed, tests prove that it would be impossible to obtain a permanently stable structure using metal filaments braided after they have been subjected to a thermical hardening, as suggested. Such an endoprosthesis would be brittle or at least unstable, the pre-stiffened wire being unable to bend plastically at their crossing points. Furthermore, a property described as basic in U.S. Pat. No. 5,718,159 is the fact that the endoprosthesis should be impervious.

Results based on recent clinical studies have shown that, in the case of an aneurysm of the abdominal aorta, 70% of the pressure wave is transmitted to the wall of the aneurysm via the endoprosthesis. (Reference: *Communication at the 27th Global Vascular Endovascular Issues Techniques Horizons*™ Nov. 16-19, 2000, page V5.1). These findings are not surprising because haemodynamics teach us that when the walls are thin, the necessary work implied for the transport of the blood increases. It is also known that when the vessels are too large, the volume of blood increases beyond what is necessary. These factors promote aneurysms.

In the case of the Superficial Femoral Artery and of the popliteal arteries, one has also to take into consideration the fact that they move in multiple plans during the limb motion in 3D directions. These arteries are thus not only compressed and rotated, but they are also shortened and extended in response to the movement. All these factors are known to negatively impact the long-term use of stents.

This shows that more stable and more robust structures have to be developed. Investigations based initially on the above consideration revealed that a far more important field of possibilities had been neglected by the searchers, namely the influence of the stents on the haemodynamic in blood vessels in general cases as well as in the particular case of aneurysms.

SUMMARY OF THE INVENTION

The above problems are solved in the stent of the invention in that it is formed of a stabilized braided framework, comprising a plurality of interconnected layers, each of these layers being interlaced to form a lattice, the mechanical characteristics of the layers being so that when in place, an outermost layer applies against the wall of a vessel wall, the other layers extending substantially along cylindrical surfaces distinct from the outermost layer so as to form a multi-layer mat locally affecting the haemodynamic of the flow of blood passing along and through said mat.

A main advantage of the present multi-layer framework is that it completely changes the haemodynamic properties of the side wall. Due to its particular porosity, it transforms the haemodynamic convection of the flow passing along it into a laminated diffusion flow passing through it, which reveals advantageous, particularly in the case of aneurysms. It also transforms the flow derivated towards a branch from turbulent to laminated, which impedes the forming of aneurysms. Finally, it avoids low shear stress flow along the wall of the covered vessel, preventing hyperplasia.

The multilayer stent has further physical and mechanical advantages over the other, single-layer, braided stents. It has the benefit of increased radial strength, a stability over a longer period of time, and better adaptation, due to the number of layers, to the type of artery and its pathology.

The structure preferably uses a single type of material, e.g. metal, ensuring its robustness and homogeneity.

In the case of a metal framework, the wires are preferably chosen from among the following materials [Phynox®, Elgiloy®, titanium and its alloys, Nitinol]. After the braiding stage, the metal wires of the stent according to the invention undergo heat treatment to impart them a hardening and a possible phase transition (giving them the required structural stability, rigidity and hoop strength), (in contrast to the hybrid stents of Thompson cited above wherein the heat treatment takes place before the braiding stage).

It is in fact commonly acknowledged that any wire which has been hardened by heat treatment loses its elasticity and its plastic deformation and that consequently it becomes rigid. It is thus strongly inadvisable to re-work a wire hardened by heat treatment, as is the case in the above hybrid stent: the heat treatment is impossible to apply a posteriori, in the presence of textile fibres which would melt or burn. According to an advantageous embodiment, the framework comprises wires of different thicknesses.

The thickness of the wires can lie within the range of between 25 and 80 microns. The advantage of using thicker wires is that they afford a better hold against the wall of the vessels and allow the endoprosthesis to withstand, without damage, the various stresses to which the vessels are subjected, especially in the areas of the neck and the knee.

The use of interconnected layers also solves the thorny issue of correlating three critical problems not solved by the prior art: using sheets of wires with materials having different mechanical characteristics or structures made from assembled modules, it is found that the endoprostheses of the prior art (principally those intended for aneurysms) have a tendency to migrate longitudinally, to change shape over time, and to degrade.

Conversely, in a prosthesis according to the invention, the mechanical properties of the wires of the different plies can be balanced in such a way as to perfectly compensate each other and ensure long-term stability.

BRIEF DESCRIPTION OF THE DRAWINGS

Other features and advantages of the invention will become evident from the following description of particular embodiments of the invention, reference being made to the attached drawings in which:

FIG. 3 is a diagrammatic view showing the use of a stent according to the invention in a carotid artery;

FIGS. 4 and 5 show the reduction of an aneurysm with the stent according to the invention;

FIG. 6 to 9 are enlarged diagrammatic views of the flow in a collateral artery, under various circumstances;

FIGS. 10 and 11 are sketches of an aneurysm with collateral, after placement of a stent according to the invention;

DETAILED DESCRIPTION OF THE INVENTION

Figure 1:
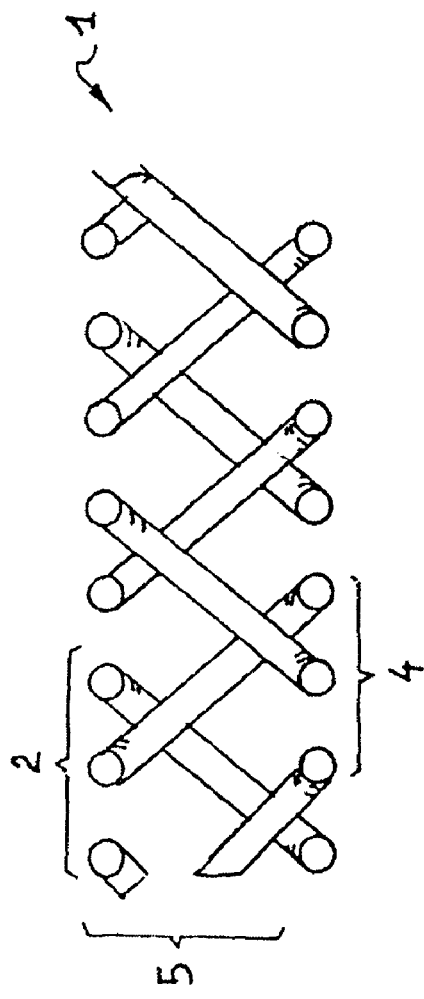
FIG. 1 is a side view of a traditional braided stent framework.
Figure 2:
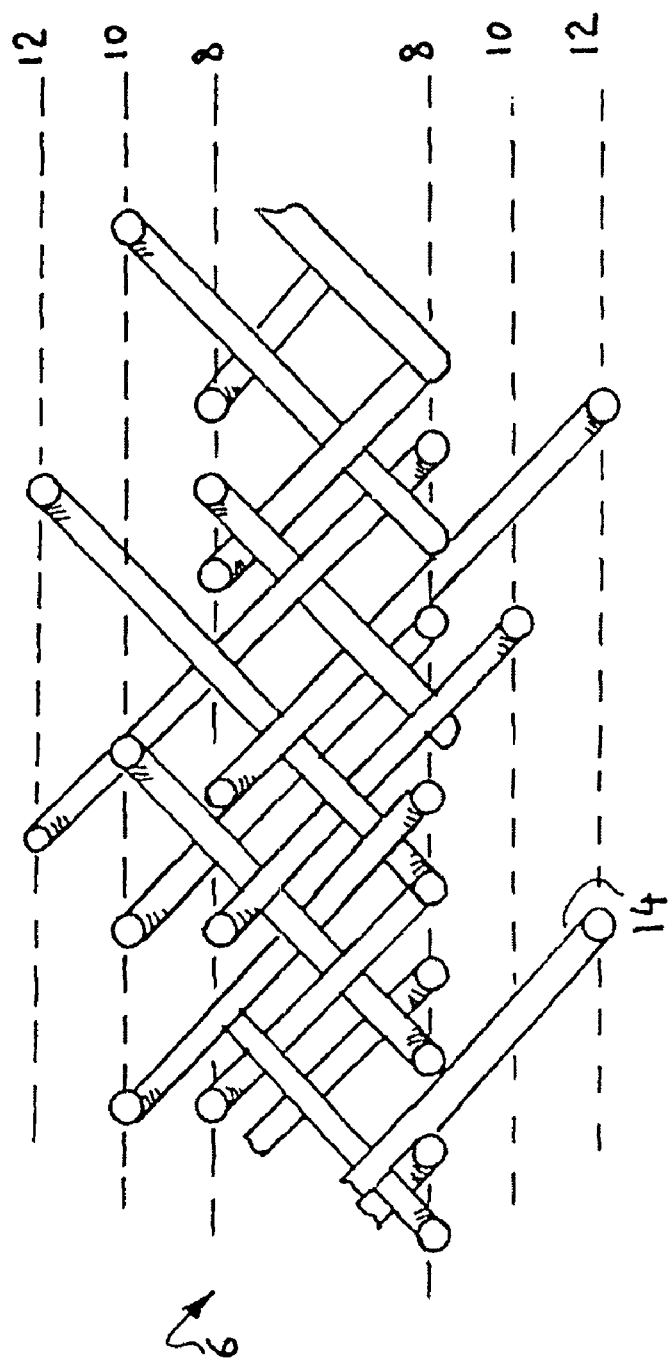
FIG. 2 is a simplified diagrammatic view of the stent multilayer framework according to the invention.

The traditional braided framework 1 is made up of a simple braid, two plies 2, 4 of wires, which are dextrogyratory 2 and laevogyratory 4, respectively, intersecting to form a simple braid 5.

The framework 6 of the invention is a multiple braid which comprises, in the example shown, three layers 8, 10, 12 whose plies are not distinct: at the time of braiding, a given number of wires 14 of the plies of the first layer 8 are interlaced with the plies of the second layer 10 and/or of the third layer 12, forming a complex lattice (this applies to the figure shown, but it goes without saying that the interlacing can continue to the $N^{th}$ layer if the number of layers is N). The wires used for forming the braid being free of any heat treatment, they comply easily to the twisting and bending imposed by the braiding process. After braiding, the layers are stabilized by a heat treatment that freezes the relative position of the wires in each layer. This manner of proceeding opens up enormous possibilities for adjusting the characteristics of the framework. Not only does it permit a wide variety of "standards" depending on the organs involved, it also in practice permits adjustment case by case by acting on the pitch of the braid, the diameter and the nature of the wires 14, the density of the braiding, the number of layers 8, 10, 12, the number of wires 14 of different diameters, and the interlacing of the layers.

It would of course be pointless citing all these advantages if the endoprostheses equipped with such a framework could not be implanted using existing equipment. However, one of the unexpected aspects of the invention is that, despite the large number of wires 14 used, the thickness of the successive layers 8, 10, 12 and the complexity of the structure, the exclusively metal multiple braid can be very easily reduced to a diameter comparable to that of a traditional framework 1. Unlike the wires or strands of the composite multi-layer frameworks or even single-layer frameworks, those of the present multilayer framework tend to occupy the space in a more effective way, probably by virtue of the complex interpenetration of the layers. It is therefore easily possible to use a conventional introducing instrument to implant a stent equipped with the novel structure, even in vessels of small diameter.

Moreover, the stent according to the invention can, after deployment, assume very large diameters (especially for an aortic dissection or in the case of thoracic aneurysms) without risk of crushing.

The present structure also allows the layers 8, 10, 12 formed of wires 14 of different diameters to act in synergy. Clinical trials conducted by practitioners (surgeons, radiologists and cardiologists) in which two stents 1 of different characteristics have simply been introduced one within the other have had mixed results or have failed, whereas the present structure 6 significantly increases the resistance to crushing without reducing flexibility.

This characteristic is important particularly in the treatment of aneurysms. This is because, over the course of time, an aneurysm tends to shorten in the longitudinal direction. A classical stent placed in these circumstances will tend to undulate and finally crush, which is not the case with the present structure.

Moreover, as has been mentioned above, the multilayer structure 6 permits the use of wires of very fine diameter which can act to adjust the required porosity, in combination with thicker strengthening wires.

The interlacing of these wires provides for a regular spatial distribution, ensuring a regular meshwork. The importance of this point will be discussed hereafter.

In addition to their inherent mechanical characteristics, it is also possible to make advantageous use of the particular features imposed on the wires by appropriate technical treatment.

It is also possible to take advantage of the use of Nitinol wires, such as are described in the application PCT/BE98/00076, to achieve reinforcement of the structure after it has been implanted.

FIG. 3 shows that, in addition to acting as a classical stent, the stent according to the invention can be successfully positioned at a site thought dangerous, for example the carotid bifurcation. The framework according to the invention makes it possible to manufacture stents which go from 6 to 50 mm in diameter; it is therefore safer and easier to place the stent—diameter preferably 25 to 40 mm—in the aortic arch 15 opposite the subclavian and vertebral arteries. It is thus possible to avoid the problem of embolisms upstream of the carotid artery more easily in terms of deployment, and more appropriately in terms of safety. A further advantage will be described hereinbelow.

The use of the multilayer structure and of metal wires whose diameter is between 25 µm and 80 µm permits realization of a structure which is both stable and effective. The three-dimensional structure of the filter allows the body's defence mechanisms to attack and efficiently "digest" possible debris before the latter causes obstruction.

FIGS. 4 and 5 illustrate the possibility of using the stent according to the invention to solve, in a hitherto unconventional way, the problem caused by aneurysms.

The classical approach to reducing aneurysms 16 has hitherto involved fitting the affected vessel 18 with an endoprosthesis equipped with a leaktight polymer covering (as described e.g. by Thompson). The practically inevitable deformation of this endoprosthesis, however, leads to the gradual appearance of leaks between this endoprosthesis and the wall of the vessel 18, especially in the case of fusiform aneurysms 16. The pouch formed by the aneurysm 16 is thus subjected to the same stresses as before and ceases to resorb. It is however possible to treat aneurysms without using so-called leaktight covers. Studies (Annals of Biomedical Engineering, Vol. 25, pages 460-469; 1997) show that by implanting a stent whose walls are within a very precise range of porosity, it is in theory possible to alter the haemodynamics in an aneurysm by transforming the convection flow (as shown in FIG. 4) to a diffusion flow (see FIG. 5), which reduces the pressure in the pouch 16, so that the latter is able to resorb normally. By adjusting the number of wires, the number of layers and the size of the gaps between the wires, it is possible to obtain the required porosity with the present stent, thus opening up a practical possibility of applying the technique described above.

As stated above, this phenomenon proves to cause an unexpected beneficial effect not only in the case of aneurysms, but also when the stent is used in the more common case of a stenosed vessel. When checking a posteriori via in-vivo assessments the progress of the restenosis (blood platelet accumulation) on the walls of a vessel covered internally by a stent or an endoprosthesis according to the invention. By what was considered at the time as an unexplainable effect (which was related to the reciprocal rubbing of the wires forming the various layers of the armature), a surprising absence of restenosis was noted. The multilayer braid would therefore have an unexpected "self-cleaning" function, thereby opening up prospective new applications for this type of stent.

Another advantage exhibited by the stent of the invention over "classical" endoprostheses was also noted: frequently aneurysms are situated in proximity to collateral vessel branch-offs in a blood vessel. In this case, the placement of a covered endoprosthesisis is strictly forbidden as one runs the risk of sealing off not only the aneurysm, but also these collateral vessel. Such a phenomenon frequently also occurs with a classical uncovered stent, through which the blood stream may begin to pass without any problem, but which becomes rapidly clogged by an increasing growth of blood platelet accumulation. Surprisingly enough, such a negative effect did not take place when the stent of the invention was used, notwithstanding the fact that during the experiments, the coverage of the "classical" (i.e. monolayer) stent used as reference was identical as the coverage of the stent of the invention.

Here also, an unexpected "self-cleaning" effect was put forward but, clearly, as the effect endured throughout the tests, such a simple explanation was not sufficient. In fact, an in-depth analysis of the effects of the three-dimensional stent wall on the blood flow was required to cast new light on the origin of this phenomenon.

Blood Circulation in the Ramifications:

Ramifications—or branchings—in the blood-circulation network play an essential role in the dispatch of blood towards the various body organs, thus allowing an efficient functioning of these organs.

To ensure that every body part be supplied with an adequate blood flow, the angles of the collaterals and dimensions of the various artery stems vary according to their location. This is why ramifications are defined by parameters, e.g., the angles they form with the main arteries they branch from and their calibre according to their location.

A smooth blood circulation demands a perfect vascularisation of the blood-circulation system to the smallest details. For instance the flow, at any place but particularly at the start of the branchings and ramifications, must be able to run with minimum effort while producing the lowest possible shearing strength against blood-vessel walls.

It is known that the branching between an artery and its collateral is at its best when the angle they form is in inverse ratio to the size of the ramification: the smaller the ramification, the wider the angle. For instance, all ramifications with a diameter so small that it seems they will hardly affect the main stream, always form with the main artery an angle of approximately 90° (as in the case of renal arteries).

Where ramifications vary significantly in size but little in diameter, the main artery forms with the branches a small lateral ramification angle (e.g., angles between the deep femoral and the external iliac artery, or between the popliteal and the anterior tibial artery). However, where a major artery splits into two branches of equal diameters, then these branches form two equal angles with respect to the artery they branch from (aortic bifurcation).

Hence, blood circulation is achieved using a minimum of energy everywhere in the body, thereby supplying what is necessary and sufficient.

In spite of the general respect of these "geometrical" laws, other factors intervene, causing a kind of spontaneous disturbance in the system balance: e.g. morphology of the arteries at the branchings out (shape), individual's physiology (functioning), and blood fluidity. To these phenomena is to be added the fact that part of the main-branch blood flow changes its direction and flows into the ramifications. This change in direction induces disturbances at the inlet, which results in a turbulence that increases resistance in the blood flow, on the first few centimeters of the course.

From a purely haemodynamic point of view, it is also well known that turbulence creates local recirculation areas that promote the development of atheroma plaques in the vessels.

Clinical trials including Doppler measuring on the branches of the abdominal aorta have shown the existence of turbulences in the systolic phase.

For instance, the entry of the coeliac stem is often the site of recirculation phenomena linked to a wide angulation with the aorta; such is also the case at the level of bifurcation of common iliac arteries, of the lumbar arteries arising (in 4 pairs) from the back of the aorta, of the lower or upper mesenteric and renal arteries, of the carotid bifurcation, coronary bifurcation, etc. . . .

What is Turbulence? a Brief Explanation

As already explained, turbulences at the start of branchings out have adverse effects on the quality of blood circulation. Intuition permits to state that the shift in the course of particles toward a branching implies a loss of kinetic energy, that we call a turbulence. The smaller the vessel's diameter, the stronger the turbulence.

Generally speaking, the blood particles that are not deviated follow their course with a lesser constraint or stress parameter, i.e. a lower or normal Reynolds (Re) number (Re being a dimensionless number built like the ratio between inertia strength and dissipation strength or viscosity strength) compared with the particles deviated toward the branch. Consequently, the flow of these particles gradually loses its stability while the Re number is increasing, until reaching a critical $Re_{critical}$ value beyond which starts an instable and dissipative—hence irreversible—turbulent system.

On the other hand, this energy loss appears in the form of vibrations that cause a murmur that might even be audible with a stethoscope.

Multi-Layer Stent and Turbulence

Theoretical simulation and tests on animals have shown, after injection of a contrast medium, a significant flow difference in the collaterals, before and after implanting a stent according to the invention. This difference is characterized by a better flow circulation in the branches after the stent has been placed. All explants have shown after one month that the improved flow is maintained, whatsoever the size of the ramification.

In vivo tests reveal that the configuration proposed by the invention, i.e. a multilayer braid where the various layers are superposed one on top of the other and further mutually offset, affords the stent used a significant role in the alteration of the stream, particularly (but not only) in the case of aneurysms wherein the blood finally stagnates, favouring haemostasis which essentially involves the blood platelets (thrombocytes). This finding is a priori entirely paradoxical, since this phenomenon does not appear when a monolayer stent is used, notwithstanding the fact that the coverage of this monolayer stent [surface area of the neck/surface area occupied by the mesh cells] is identical in both cases.

To demonstrate this point, we have used a stent of porosity equivalent to that of a monolayer stent (that is to say about 70 to 80%) but using a different three-dimensional arrangement of the pores and the layers so as to obtain an adequate permeability, sufficient to attenuate the force that the vortices create when forming immediately upon entry into the aneurysm.

The permeability to water is defined as the quantity of water (in $gr/min.cm^2$) passing into a standardized apparatus under a pressure corresponding to 120 mmHg, (ISO 7189: 1998,§8.2.2). In this instance, without the stent the value reaches 14 260 $gr/min.cm^2$ (which corresponds thus to a porosity of 100%) and with a 3 mm stent is of the order of 12 162±76 $gr/min.cm^2$, (which corresponds to a porosity of 85%).

The "porosity" is therefore objectively of the same order of magnitude as that of a monolayer stent (for example of the type of a tube sectioned by laser, or braided).

The results that were obtained are shown at FIG. 6 to 9.

FIG. 6 displays an enlarged diagram of the velocity of blood (represented vectorially by arrows) obtained in the mouth 19 of a collateral 20 opening up into a main vessel 18 when in "natural state" (thus, without any stent). An important whirlpool 22 is visible near the center of the collateral 20 and the speed of the blood is increased towards one of the walls of the collateral. The flow disturbance disappear only at the top of the diagram, thus (relatively) far from the "mouth" 19.

FIG. 7 displays the same site, in the case when a single-layer stent 1 is placed along the main vessel. The whirlpool 22 is reduced, but the flow nevertheless remains perturbated along the same distance in the collateral 20.

At FIG. 8, the single-layer stent has been replaced by a double-layer stent 6 (represented by two rows 10, 12 of square dots) with irregular meshes. The back flow has almost disappeared, but a difference of pressure is still visible between the uphill and the downhill sides of the mouth 19 of the collateral 20.

Figure 9:
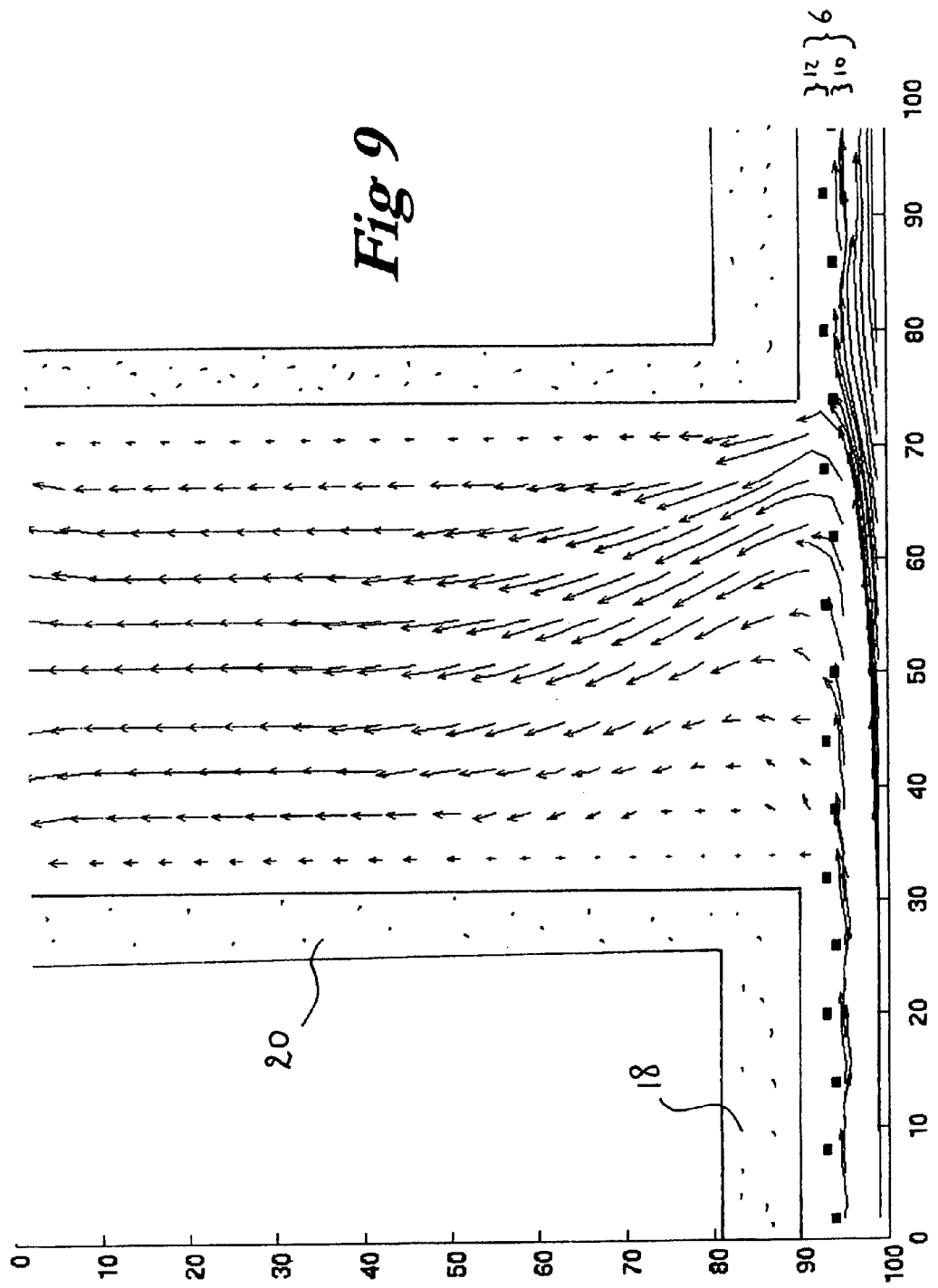

FIG. 9 still displays the same site, but in this case, the meshes of the superponed layer 10, 12 have been alined so as to obtain a regular grid. When this figure is compared with FIG. 6, the difference is tremendous: the arrows representing the flow of blood very quickly align, an evidence of the fact that the flow has been laminated, and the whirlpool 22 has completely vanished.

An explanation of this effect is that the energy-creating turbulence at the start of the branching out is converted into a great number of mutually-cancelling micro-turbulences (this level of turbulence is insignificant). This leads to a pressure drop at the inlet of the branch and consequently the velocity is increased. Furthermore, what renders the present stent more effective than others is without doubts the way according to which the meshes of its various layers are distributed in space. Stated otherwise, the modification of the three-dimensional geometry dictates the effectiveness of the stent in altering the haemodynamics and, accordingly, the possible forming or reduction of aneurysms. Hence, it is important to use a braiding process able to keep a stable configuration of the layers, as well in space as in time.

One may wonder whether this effect will disappear or remains stable as time goes by. Here also, the in vivo tests gives surprisingly good results.

Interestingly, the lasting of the permeability is linked to the fact that the multi-layer stent, unlike classical stents, is not lined with endothelium at the collateral entry area (see below: flowing against the wall).

In order to better understand this unexpected aspect of the flowing, we simulated various configurations with the stent positioned in front of a branch, using the LBM method (Lattice Boltzmann Method) and Molecular Modelization. Results confirmed what had been observed on animal models.

Effect of the Multi-Layer Stent on Parietal Flow and Link with Flow in the Collaterals The tests of a stent on the animal show, after one month, a double phenomenon A) the walls of the main vessel slowly integrate the outermost layer of the stent, with gradual formation of a permeable monofibrotic barrier with endothelial cells film on its surface. This means that the stent wires become a part of the vessel wall without inducing a further formation of plaque: the dream of all the searchers in this field.

B) the endothelial cell film is completely absent in front of the mouths of collateral vessels, leaving them completely free of clogging.

Such an observation is in agreement with the haemodynamic analyses carried out following the Computational Fluid Dynamics (CFD) method and the Lattice Boltzmann Method (LBM). These theoretical analyses demonstrate that the presence of a gap between the stent layers extending along the wall, results, in the blood elements involved, in a dynamic favourable to a reduction of intirnal proliferation. Furthermore, the lamination of the flow is related to a pressure drop at each layer (10, 12) in the mouth of the collateral and, as a secondary effect, the flow acceleration impedes the clogging of the stent layers.

To the contrary, tests carried out with a classical monolayer stent 1 (see FIG. 7) clearly show an interaction between the wall and the blood flow. This is a factor that may promote the outbreak of hyperplasia and restinosis for patients having i.a. a bad diet scheme.

Clinical Consequences and Multi-Layer Stent

Turbulence in the collateral vessels

The location of the lesions tends to show that haemodynamic phenomena (turbulence areas) play a significant part. Hence, when treating a stenosis it is paradoxically recommended to make sure that the stent of the invention properly covers the branches, in order to ensure a better blood circulation, which is an uttermost paradoxical conclusion for a man skilled in the art.

from the phenomenon described under (A), it results that there is no more necessary to cover stents with chemicals preventing the growth of plaque, which is the most preoccupying drawback of present-day stents or luminal endoprostheses Permeability of cerebral perforators As already discussed above, any known type of stents (including laser-cut type stents) does not completely eliminate flow turbulence at the start of a branching out, but it may also be that large width grid elements have been positioned exactly in front of a perforator (1-2 mm) thus choking it. Such obstructions may result in a disastrous dysfunctioning of one or several vital parts of the brains.

Thanks to its unique concept, the present multi-layer stent meets two essential requirements: ensuring an efficient flow within the perforator; avoiding the latter being obstructed. The wires of the multi-layer stent are of circular cross-section, ensuring a minimal contact surface and vary between 40 and 50 μm. Even if a wire is positioned at the start of a branching, the flow can run round it while being laminated (this issue will be addressed later on), thus ensuring a smooth blood circulation and a better dispatch into the various collaterals.

Intimal Hyperplasia in the Wall in Case of Stenosis

Figure 12:
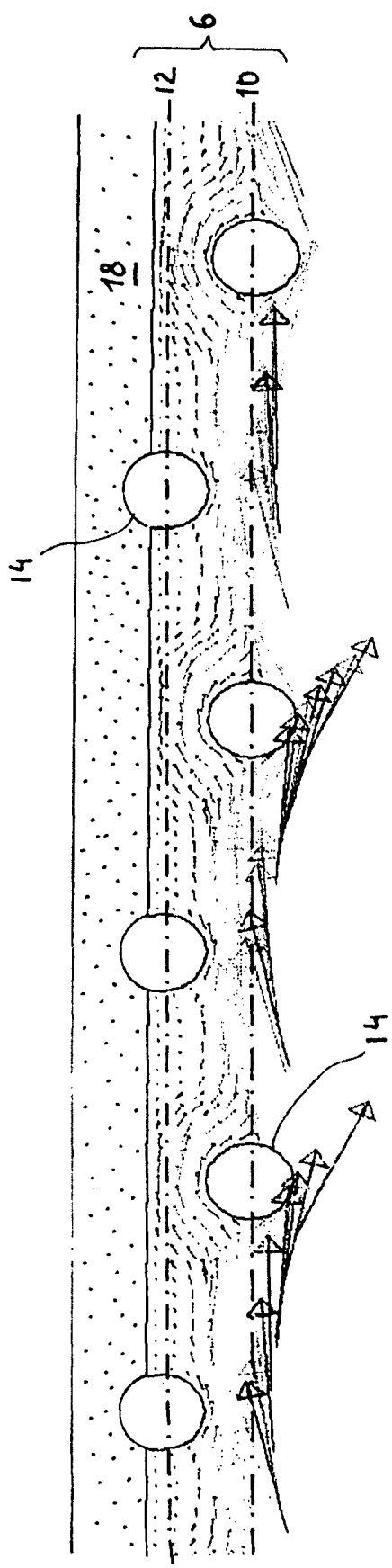
FIG. 12 is an enlarged diagrammatic view of the flow along the wall of an artery covered by a multi-layer stent of the invention.

FIG. 12 shows that the external layer 12 of a stent according to the invention in contact with the artery wall deviates the major part of the blood flow towards the center of the artery 18. This results in a reduction of the contact strength (friction) with the artery wall. The deviated, accelerated blood flow then reaches the inner layer 10 of the stent, which supports, unaffected, its strongest shearing effect. The very small part of the blood flow remaining in close vicinity of the vessel wall presents a reduced mobility. The blood particles carried by this flow quickly form several monofibrotic layers lined with a smooth layer enthothelial cells extending along the wall, covering the external layer 12 of the stent, as already stated above.

The role of this endothelial cells film is very important, because it prevents the development of lipidic striae: several studies have shown that lipidic striae precede the development of intermediary lesions affecting endothelium layers in these striae, which may cause a rupture in the wall, thus exposing the smooth muscle cells of the media to peripheral blood. The fibrous plaques then increase in volume, thus clogging the artery lumen and interfering with the blood flow. Platelets, lymphocytes and monocytes cling to these cells and liberate growth factors, e.g. PDGF, which stimulates the proliferation of muscle cells and contributes to the development of plaques.

Since the arteries wherein stents are placed are generally damaged arteries, with thick and hard atheromatous plaques, it is important to emphasize this property of the multilayer stent of the invention: as soon as positioned, it creates a barrier between the blood flow and the plaque, thus stopping the thickening process of the latter that would unavoidably clog by and by the lumen of the artery. A true physiological repair of the artery wall is thus obtained, which appears as a complete paradox for the man skilled in the art, for which the placement of a stent is deemed to unavoidably provoke a damage to the wall.

Further Effect on Aneurysms: Physiological Healing

Also it has been shown that the multiplayer stent behaves differently if the aneurysm is sacular or fusiform. In the sacular aneurysm the stent change the hemodynamic inside by alterating the global flow in the pouch. In several studies carried out by the inventor, it has been observed that regardless the neck size of the aneurysm, the stent induces a complete thrombosis.

Theoretical and clinical studies have been carried out show that the multilayer stent behaves differently in the case of the fusiform aneurysm with collateral (the collateral being borne by one side of the aneurismal pouch) as represented at FIGS. 10 and 11. The presence of multilayer stent (FIG. 11) brings the flow from a very chaotic behaviour (with recirculation zones) (as shown at FIG. 10) to a more regular or laminated flow along the pouch in the area where there is no branch (see FIG. 11). Test carried out in vivo show that a laminar flow remodels the diseased wall. Furthermore, a completely unexpected effect is observed: the laminated flow goes on supplying the collateral 20, which creates a kind of depression in the aneurysmal pouch 16, leading to a shrinking of the latter.

A method for preventing the apparition of aneurysms and curing aneurysms has thus been developed Said method comprises the following operations:

Selecting at least one bio-compatible metal;

Drawing out said at least one metal into wires;

Choosing braiding parameters so that the braid will be given a definite dynamic porosity;

Braiding said wires so as to form a multi-layer stent, the wires of each layer being interlaced with the wires of each of the other layers;

Stabilizing the form of the stent and the relative position of the wires of each layers by submitting it to a heat treatment;

Sterilizing said stent;

Inserting the stent into a vessel to de cured

Allowing the stent to deploy along the wall of the vessel and in front of possible collaterals of the vessel;

Allowing an outermost layer of the stent to rest against the wall of the vessel;

Allowing the other layers to extend substantially along cylindrical surfaces distinct from the outermost layer;

Allowing the layers to alter the haemodynamic of a flow of blood passing along or through said wall, transforming the haemodynamic convection of the flow passing along said wall into a laminated diffusion flow passing through said wall;

Allowing a drop of pressure to develop towards the outermost layer.

What is claimed is:

1. Luminal endoprosthesis consisting of a braided framework devoid of textile fibers comprising a plurality of stabilized layers of biocompatible metal wires, each layer forming a mesh, wherein the meshes are interlaced, forming a lattice with a plurality of wires of a given layer being integrated in the mesh of at least one of the adjacent layers such that meshes of adjacent layers of the framework are substantially aligned so as to be permeable to body fluids, yet offset so as to cause a pressure drop across successive layers of the framework as body fluid passes through the layers of the framework, thereby reducing flow turbulence and promoting laminated diffusion flow of body fluids.

2. Luminal endoprosthesis according to claim 1, wherein the material of the wires is selected from the group consisting of stainless steel; alloys of cobalt, chromium, and nickel; titanium, and alloys of titanium and nickel.

3. Luminal endoprosthesis according to claim 1, wherein the framework comprises wires of different metals.

4. Luminal endoprosthesis according to claim 1, wherein the thickness of the wires lies at least within a range of between 25 and 80 micrometers.

5. Luminal endoprosthesis according to claim 1 comprising at least three stabilized layers of biocompatible metal wires.

6. Luminal endoprosthesis according to claim 5, wherein at least some of the wires of at least one of the layers are integrated in the mesh of a layer that is not adjacent to the at least one of the layers.

* * * * *